(12) United States Patent
Huang

(10) Patent No.: US 7,121,404 B2
(45) Date of Patent: Oct. 17, 2006

(54) ASSEMBLED MULTI-FUNCTIONAL SHOEBOX

(76) Inventor: Yung-Kuang Huang, No. 75, Chi-Tsu St., Shulin City, Taipei Hsien (TW)

( * ) Notice: Subject to any disclaimer, the term of this patent is extended or adjusted under 35 U.S.C. 154(b) by 511 days.

(21) Appl. No.: 10/696,657

(22) Filed: Oct. 30, 2003

(65) Prior Publication Data
US 2005/0109643 A1    May 26, 2005

(51) Int. Cl.
B65D 85/18 (2006.01)
B65D 1/24 (2006.01)
A47B 77/08 (2006.01)

(52) U.S. Cl. .................. 206/278; 454/184; 312/236; 220/503; 220/504; 220/524; 220/552

(58) Field of Classification Search .............. 206/278; 454/184; 312/236, 31; 220/503, 504, 524, 220/552
See application file for complete search history.

(56) References Cited

U.S. PATENT DOCUMENTS

| | | | | |
|---|---|---|---|---|
| 2,176,140 A | * | 10/1939 | Lofgren | ...................... 422/294 |
| 3,866,994 A | * | 2/1975 | Bonin | ........................ 312/236 |
| 3,895,215 A | * | 7/1975 | Gordon | ...................... 219/400 |
| 4,014,598 A | * | 3/1977 | Stalley et al. | ............... 312/236 |
| 4,420,678 A | * | 12/1983 | Kalb | .......................... 219/387 |
| 4,452,500 A | * | 6/1984 | Zlotnik | ....................... 312/236 |
| 4,753,496 A | * | 6/1988 | Bussard | ..................... 312/236 |
| 6,213,866 B1 | * | 4/2001 | Impellizzeri | ............... 454/184 |

* cited by examiner

Primary Examiner—Tri M. Mai
(74) Attorney, Agent, or Firm—Lowe Hauptman & Berner, LLP

(57) ABSTRACT

An assembled multi-functional shoebox comprises at least one rectangular box body. The rectangular box body further comprises a frame having a cruciform structure with each end having a right-angled isosceles triangle supporting plate; an upper cover firmly secured to an upper end of the frame; a lower cover firmly secured to a lower end of the frame; a plurality of doors between the upper cover and lower cover; a supporting plate; a hollow short shaft being protruded from the supporting plate; the supporting plate being rotatable; a seat being a drawer; a steel ball bearing being a center of the seat; a fan being installed below the bearing; a heat dissipating device and an ozone generator being supported by a supporter; a drawer for placing liquid, powdered deodorants, aromatics, the drawer having a plurality of small chambers arranged around a space of the seat.

7 Claims, 4 Drawing Sheets

US 7,121,404 B2

ASSEMBLED MULTI-FUNCTIONAL SHOEBOX

FIELD OF THE INVENTION

The present invention relates to shoeboxes, and particular to an assembled multi-functional shoe-box, in that shoebox is rotatable, and the doors are at four sides of the shoebox so that objects can be taken out from any side. Moreover, shoes in the shoebox can be dried, sterilized, and perfumed.

BACKGROUND OF THE INVENTION

Generally, conventional shoeboxes have only one side having a door for taking shoes so that the user is inconvenient as he or she takes shoes from the shoebox. If there are many people using the shoebox at the same time, then the inconvenience is more apparent. Moreover, generally conventional shoeboxes cannot be rotated so that users must walk to the side having a door. Moreover, since the shoes often have germs therein, or emits undesired odor, or are wet. These are unacceptable to the users. However, the conventional shoebox has no function of drying, sterilizing and perfuming.

Thereby, there is an eager demand for a novel shoebox which can improve the above-mentioned prior art defects.

SUMMARY OF THE INVENTION

Accordingly, the primary object of the present invention is to provide an assembled multi-functional shoebox, wherein the shoebox is rotatable and doors are at four sides of the shoebox so that objects can be taken out from any side.

Another object of the present invention is to provide an assembled multi-functional shoebox, wherein shoes in the shoebox can be dried, sterilized, and perfumed.

To achieve above object, the present invention provides an assembled multi-functional shoebox comprises at least one rectangular box body; the rectangular box body further comprises a frame having a cruciform structure with each end having a right-angled isosceles triangle supporting plate; an upper cover firmly secured to an upper end of the frame; a lower cover firmly secured to a lower end of the frame; a plurality of doors between the upper cover and lower cover; a supporting plate; a hollow short shaft being protruded from the supporting plate; the supporting plate being rotatable; a seat being a drawer, a steel ball bearing being a center of the seat; a fan being installed below the bearing; a heat dissipating device and an ozone generator being supported by a supporter; a drawer for placing liquid, powdered deodorants, aromatics, the drawer having a plurality of small chambers arranged around a space of the seat.

The various objects and advantages of the present invention will be more readily understood from the following detailed description when read in conjunction with the appended drawing.

DETAILED DESCRIPTION OF THE INVENTION

In order that those skilled in the art can further understand the present invention, a description will be described in the following in details. However, these descriptions and the appended drawings are only used to cause those skilled in the art to understand the objects, features, and characteristics of the present invention, but not to be used to confine the scope and spirit of the present invention defined in the appended claims.

Figure 1:
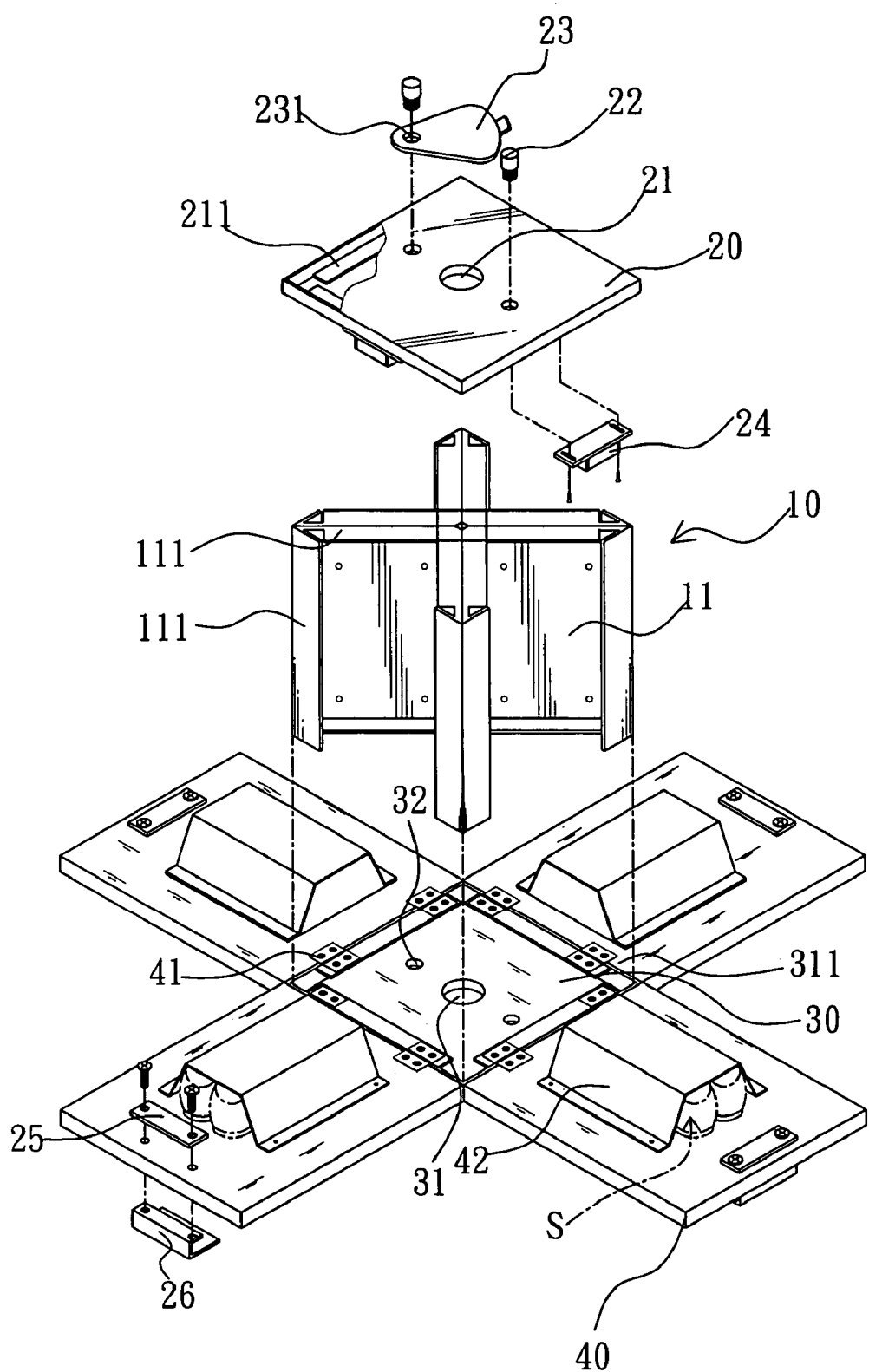
FIG. 1 is an exploded perspective view of the present invention.
Figure 2:
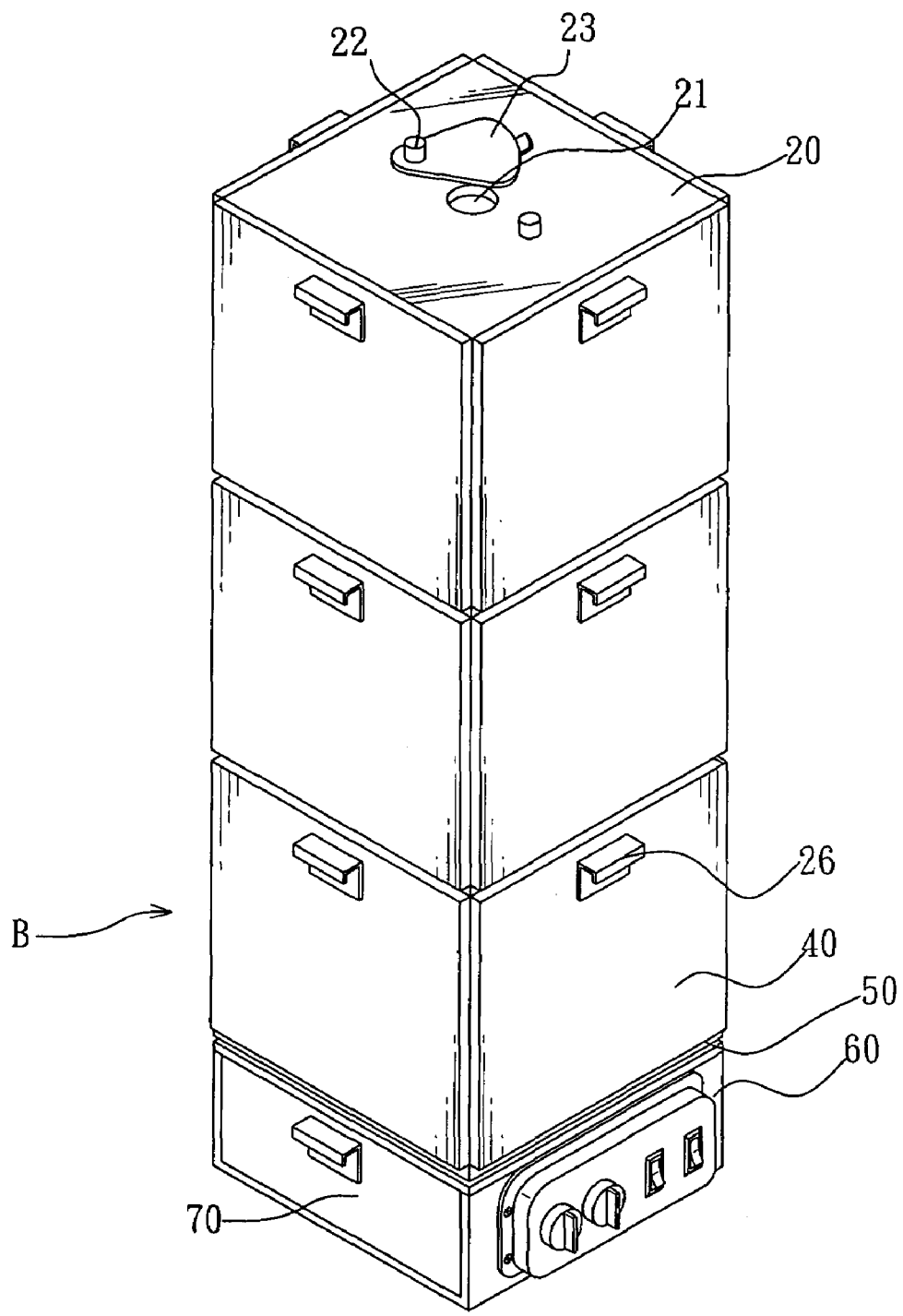
FIG. 2 is an assembled perspective view of the present invention.

With reference to FIGS. 1 and 2, the assembled multi-functional shoebox of the present invention is illustrated. The assembled multi-functional shoebox includes at least one rectangular box body B. The rectangular box body B has the following components.

A frame 10 has a cruciform structure with each end having a right-angled isosceles triangle supporting plate 11.

An upper cover 20 is firmly secured to an upper end of the frame 10.

A lower cover 30 is firmly secured to a lower end of the frame 10. The lower cover 30 has two pinholes 32.

Four doors 40 are between the upper cover 20 and lower cover 30. A lower end of each door 40 has two hinges 4d. The hinges 41 are connected with the lower cover 30. An inner surface of each door 40 has a shoe cartridge 42. A lower end of each shoe cartridge 42 is sealed and an upper end of the shoe cartridge 42 is opened (referring to FIG. 1).

Figure 3:
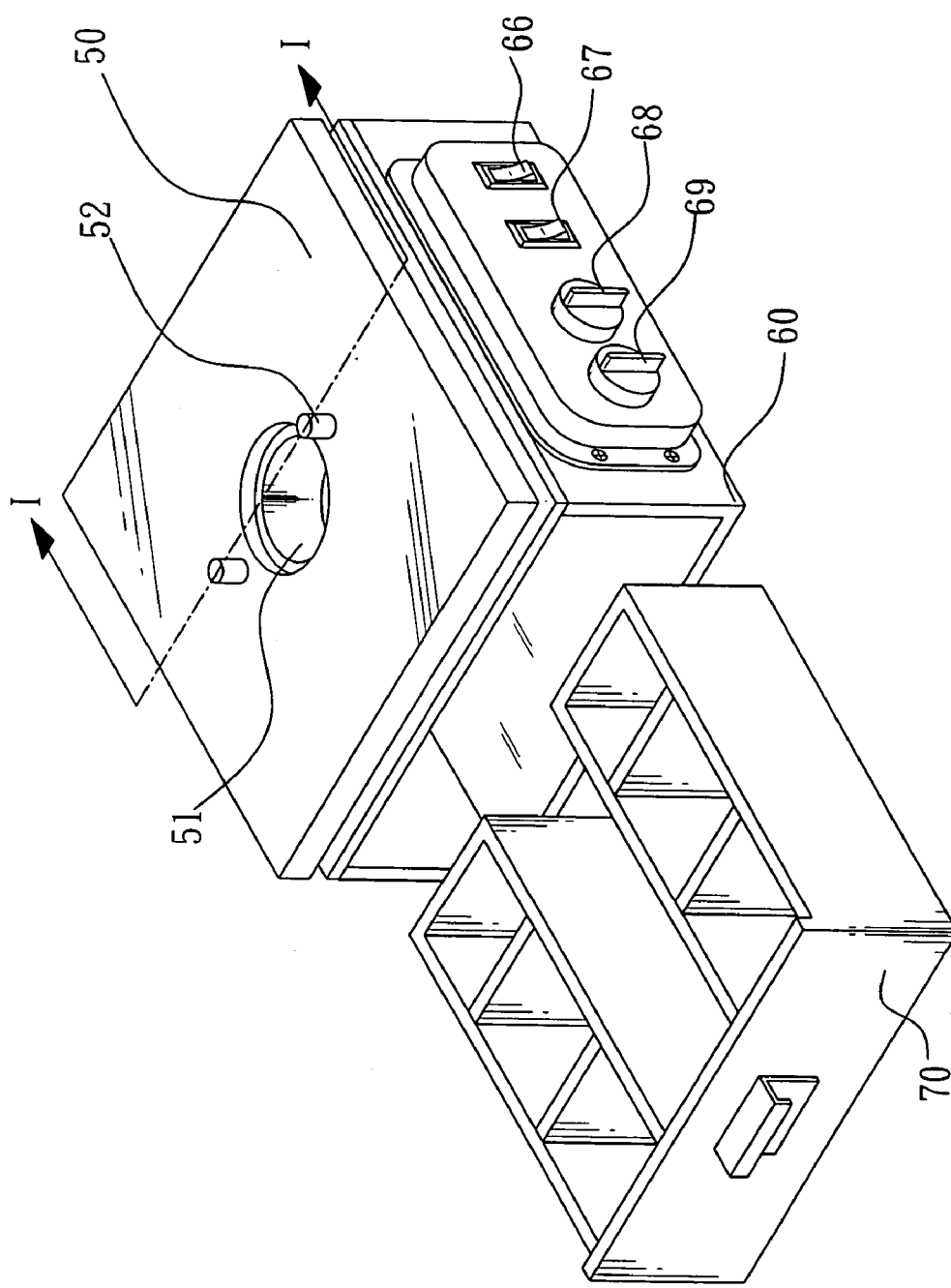
FIG. 3 is a perspective view of the seat of the present invention.
Figure 4:
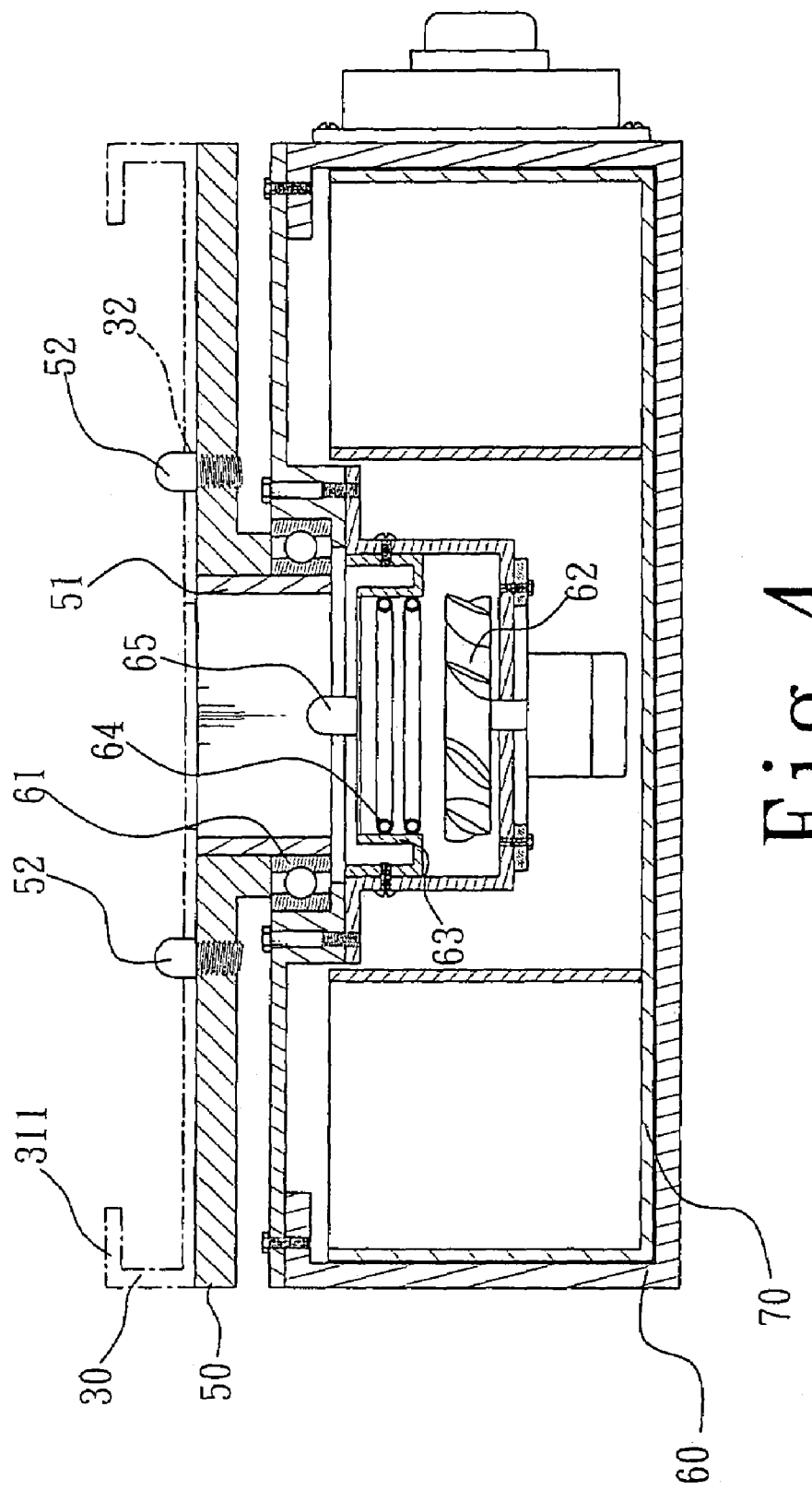
FIG. 4 is a cross section view along line I—I of FIG. 3.

A supporting plate 50 serves to support the shoebox and is a rectangular plate. A size of the supporting plate 50 is identical to that of the lower cover 30. A hollow short shaft 51 is protruded from the supporting plate 50. A hollow portion of the hollow short shaft 51 is as a ventilating hole. Two positioning pins 52 are protruded from the supporting plate 50 and are positioned with respect to the pinholes 32 of the lower cover 30 (referring to FIGS. 3 and 4).

A seat 60 is below the supporting plate 50 and has an inner space. A steel ball bearing 61 is around a center the inner space of the seat 60. The bearing 61 supports the short shaft 51 of the supporting plate 50. Thereby, the shoebox above the supporting plate 50 is rotatable. A fan 62 is installed below the bearing 61. A supporter 63 is installed above the fan 62 and below the bearing 61. A heat dissipating device 64 and an ozone generator 65 are supported by the supporter 63. A lateral side of the seat 60 has a power switch 66, an ozone generating switch 67, a temperature controlled switch 68, a timer 69, etc.

A drawer 70 serves for placing liquid, powdered deodorants, aromatics, etc. The drawing has a plurality of small chambers arranged around space of the seat which receives the fan 62, the heat dissipating device 64 and the ozone generator 65.

A center of the upper cover 20 is installed with a vent hole 21. Two sides of the vent hole 21 are installed with respective positioning pins 22. A ventilating control plate 23 has a round hole 231. One of the positioning pins 22 is inserted into the round hole 231 so that the ventilating control plate 23 is movable for controlling the opening of the round hole 21 so as to control the air ventilation from the round hole 21.

Four edges of the upper cover 20 are folded inwards as folded edges 211. Each folded edge 211 is installed with a magnet or hook 24 for coupling a metal sheet 25 on an inner side of one respective door 40. An outer side of each door 40 is disposed with a handle 26 (referring to FIG. 1).

A center of the lower cover 30 is installed with a ventilating round hole 31 identical to the round hole 21 of the upper cover 20 and two positioning pins 22 with respect to the pinholes 32 of the lower cover 30. Thereby, by the connections of the pinholes 32 and the positioning pins 22, a plurality of box bodies B can be assembled as a whole shoebox (referring to FIG. 2).

ASSEMBLY OF THE PRESENT INVENTION

Referring to FIG. 1, in assembly, a cruciform frame 10 with four right-angled isosceles triangle supporting plates 11 is formed. Each lateral edge of each right-angled isosceles triangle supporting plate 11 is folded inwards as folded edges 111.

Each of four sides of the upper cover 20 is folded inwards as an upper cover folded side 211 and each of four sides of the lower cover 30 is folded inwards as a lower cover folded side 311.

The upper cover 20 is installed above the frame 10 and the lower cover 30 is installed below the frame 10 so as to form a box. Thereby, each box body B has four triangular spaces.

A lower end of each door 40 has two hinges 40. The hinges 41 are connected with the lower cover 30. An inner surface of each door 40 has a shoe cartridge 42. A lower end of each shoe cartridge 42 is sealed and an upper end of the shoe cartridge 42 is opened. Shoes S are placed in the shoe cartridge 42. When the door 40 is closed, and shoes are uprightly arranged in one triangular space.

When the door 40 is closed, the metal sheet 25 at the inner side of the door is coupled with the magnet or hook 24 on the upper cover 20 so as to fix the door 40 the box body B. The handle 26 is at an upper side of the door 40 so that the user can handle the door easily.

FUNCTIONS OF STERILIZING, PERFUMING AND DRYING

Moreover, the present invention has functions of sterilizing, perfuming, and drying.

In the present invention, each of the upper cover 20, lower cover 30, hollow short shaft 51 of the supporting plate 50 is installed with a ventilating round holes 21. All the ventilating round holes 21 has the same inner diameter.

The supporting plate 50 is a rectangular plate. The size of the supporting plate 50 is identical to that of the lower cover 30. The hollow short shaft 51 is protruded from the supporting plate 50. A hollow portion of the hollow short shaft 51 is as a ventilating hole. The two positioning pins 52 are protruded from the supporting plate 50 and are positioned with respect to the pinholes 32 of the lower cover 30 (referring to FIGS. 3 and 4). Since the area of the supporting plate 50 is identical to that the lower cover 30, the stability of the assembled multi-functional shoebox is preferred.

The steel ball bearing 61 is around a center of the seat 60. The bearing 61 supports the short shaft 51 of the supporting plate 50. Thereby, the shoebox above the supporting plate 50 is rotatable. The fan 62 is installed below the bearing 61. The supporter 63 is installed above the fan 62 and below the bearing 61. The heat dissipating device 64 and the ozone generator 65 are supported by the supporter 63. The lateral side of the seat 60 has the power switch 66, the ozone generating switch 67, the temperature controlled switch 68, the timer 69, etc.

The drawer 70 has a center space for receiving the fan 62, the heat dissipating device 64 and an ozone generator 65. The drawer 70 has a plurality of small chambers arranged around the center space for placing liquid, powdered deodorants, aromatics, etc.

By above construction, the present invention has the function of sterilizing, perfuming and drying.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An assembled multi-functional shoebox comprising at least one rectangular box body; the rectangular box body further comprising:
    a frame having a cruciform structure with each end having a right-angled isosceles triangle supporting plate;
    an upper cover firmly secured to an upper end of the frame;
    a lower cover firmly secured to a lower end of the frame;
    a plurality of doors between the upper cover and lower cover; a lower end of each door having hinges for being connected to the lower cover;
    a supporting plate being a rectangular plate with a size identical to that of the lower cover; a hollow short shaft being protruded from the supporting plate; the supporting plate being rotatable;
    a seat having an inner space; a bearing being arranged around a center the inner space of the seat; the bearing supporting the short shaft of the supporting plate so that the shoebox above the supporting plate is rotatable; a fan being installed below the bearing, a supporter being installed above the fan and below the bearing; a heat dissipating device and an ozone generator being supported by the supporter;
    a drawer within the seat for placing liquid, powdered deodorants, aromatics, the drawer having a plurality of small chambers arranged around the inner space of the seat which receives the fan, the heat dissipating device and the ozone generator.

2. The assembled multi-functional shoebox as claimed in claim 1, wherein a center of the upper cover is installed with a vent hole; two sides of the vent hole are installed with respective positioning pins; a ventilating control plate has a round hole; one of the positioning pins is inserted into the round hole of the ventilating control plate so that the ventilating control plate is movable for controlling the opening of the round hole so as to control the air ventilation from the round hole.

3. The assembled multi-functional shoebox as claimed in claim 1, wherein an inner surface of each door has a shoe cartridge for receiving shoes.

4. The assembled multi-functional shoebox as claimed in claim 1, wherein a center of the lower cover is installed with a ventilating round hole identical to the round hole of the upper cover and two positioning pins with respect to the pinholes of the lower cover; thereby, by the connections of the pinholes and the positioning pins, a plurality of box bodies can be assembled as a whole shoebox.

5. The assembled multi-functional shoebox as claimed in claim 1, wherein a hollow short shaft is protruded from the supporting plate; a hollow portion of the hollow short shaft is as a ventilating hole communicated to the round hole of the lower cover; the hollow short shaft is supported by the bearing so that the supporting plate is rotatable.

6. The assembled multi-functional shoebox as claimed in claim 1, wherein the bearing is around a center of the seat; a fan is installed below the bearing; a supporter is installed above the fan and below the bearing; a heat dissipating device and an ozone generator are supported by the supporter; a lateral side of the seat has a power switch, and an ozone generating switch.

7. The assembled multi-functional shoebox as claimed in claim 1, wherein two sides of the drawer have a plurality of smaller chambers.

* * * * *